United States Patent [19]

Imai

[11] 4,418,237

[45] Nov. 29, 1983

[54] DEHYDROGENATION OF DEHYDROGENATABLE HYDROCARBONS

[75] Inventor: Tamotsu Imai, Mount Prospect, Ill.

[73] Assignee: UOP Inc., Des Plaines, Ill.

[21] Appl. No.: 380,796

[22] Filed: May 21, 1982

Related U.S. Application Data

[63] Continuation-in-part of Ser. No. 248,731, Mar. 30, 1981, abandoned.

[51] Int. Cl.$^3$ .............................................. C07C 5/333
[52] U.S. Cl. ................................... 585/443; 585/441; 502/328
[58] Field of Search ................... 252/466 A; 585/441, 585/443, 444, 445

[56] References Cited

U.S. PATENT DOCUMENTS

| | | | |
|---|---|---|---|
| 3,380,931 | 4/1968 | Ryland | 252/432 |
| 3,437,703 | 4/1969 | Reitmeier et al. | 585/443 |
| 3,437,703 | 4/1969 | Reitmeier et al. | 260/669 |
| 3,849,343 | 11/1974 | Hoekstra | 252/466 |
| 3,855,330 | 12/1974 | Mendelsohn et al. | 585/441 |
| 3,855,330 | 12/1974 | Mendelsohn | 260/669 |
| 3,972,952 | 8/1976 | Clark | 252/466 |
| 4,048,245 | 9/1977 | Pollitzer et al. | 252/466 |
| 4,169,815 | 10/1979 | Drehman | 252/466 |
| 4,199,436 | 4/1980 | Courty | 252/466 |

Primary Examiner—W. J. Shine
Attorney, Agent, or Firm—James R. Hoatson, Jr.; Raymond H. Nelson; William H. Page, II

[57] ABSTRACT

Dehydrogenatable hydrocarbons may be subjected to a dehydrogenation process in which a dehydrogenatable hydrocarbon is contacted with a dehydrogenation catalyst at dehydrogenation conditions in the presence of steam. The resulting mixture of undehydrogenated dehydrogenatable hydrocarbon, dehydrogenated hydrocarbon, hydrogen and steam is contacted with an oxygen-containing gas in the presence of an oxidative catalyst comprising a noble metal of Group VIII of the Periodic Table and a metal cation which possesses an ionic radius no less than about 1.35 Angstroms composited on a porous alumina support.

10 Claims, No Drawings

DEHYDROGENATION OF DEHYDROGENATABLE HYDROCARBONS

CROSS-REFERENCE TO RELATED APPLICATIONS

This application is a continuation-in-part of my copending application, Ser. No. 248,731 filed Mar. 30, 1981 and now abandoned, all teachings of which are incorporated herein by reference thereto.

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogenatable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc. may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene since at equilibrium conditions, only undesirable side reactions continue to take place. Therefore, it is necessary to maintain the desired temperature level in order to provide a high equilibrium conversion level and a high reaction rate. In the conventional processes, the maintenance of temperature is attained by reheating the product stream with the addition of superheated steam between dehydrogenation catalyst beds using a multicatalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated steam. One method of providing for the maintenance of the reaction temperature is to introduce oxygen into the reaction mixture by way of oxygen or an oxygen-containing gas such as air which will burn the hydrogen formed during the reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and higher styrene selectivity are achievable.

The selective combustion of hydrogen with the oxygen in the oxygen-containing gas requires the presence of an oxidation catalyst. There are some key requirements for the oxidation catalyst to be usable for such a purpose. The most important catalytic property required is good catalytic stability since the oxidation catalyst must survive under very severe reaction conditions, namely at about 600° to 650° C. in the presence of steam. Under such conditions, porous inorganic materials such as aluminas, silicas and zeolites cannot maintain their pore structures for a long period of time, resulting in the permanent damage of catalysts prepared using such materials as supports, e.g. platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene production.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide and from 8% to 10% of potassium oxide. In addition, another dehydrogenation catalyst which is employed comprises a mixture of nickel, calcium, chromic oxide, graphite with a major portion of a phosphate radical. In addition to these dehydrogenation catalysts, the reaction also employs a catalyst for the oxidation step of the process comprising platinum or palladium in elemental form or as a soluble salt. Another U.S. patent, namely, U.S. Pat. No. 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metals or metalloids such as lead, silver, tin, manganese, phosphorus, silicon, boron and sulfur.

U.S. Pat. No. 3,855,330 discloses a method for the production of styrene in which ethylbenzene is treated in the vapor state by passage over a dehydrogenation catalyst and an oxidation catalyst while introducing oxygen into the reaction medium. The dehydrogenation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular sieves of the zeolite type which have been charged with ferrous, heavy or noble metals. The patent lists the types of catalysts which are employed including copper or various zeolites, platinum on alumina, platinum on spinel, platinum and sodium on zeolites, platinum, sodium, and potassium on zeolites, etc.

In a process for the dehydrogenation of dehydrogenatable hydrocarbons wherein said hydrocarbons are treated with steam and a dehydrogenation catalyst along with a subsequent or concurrent treatment with an oxygen-containing gas in the presence of an oxidation catalyst, it will hereinafter be shown that by utilizing a catalyst of the type of the present invention, it is possible to obtain the desired product in an excellent yield with a concomitant use of the catalyst for a longer period of time due to the excellent stability of the catalyst during the reaction period.

BRIEF SUMMARY OF THE INVENTION

This invention relates to a process for the dehydrogenation of dehydrogenatable hydrocarbons utilizing a catalyst which is highly active and selective with particular emphasis on catalytic stability when utilized in an oxidation reaction. The catalyst, which is termed an oxidation catalyst, is used in conjunction with a dehydrogenation catalyst which is employed in a process for the dehydrogenation of a dehydrogenatable hydrocarbon. As will hereinafter be shown in greater detail, by utilizing this catalytic composition of matter, it is possible to obtain dehydrogenatable hydrocarbons in a relatively high yield while maintaining the stability and activity of the catalyst, thereby obviating the necessity for regenerating or changing the catalyst and thus adding to the economical feasibility and attractiveness of a dehydrogenation process. In addition to maintaining the activity of the catalyst, the catalyst will also exhibit a selectivity toward hydrogen rather than to carbon dioxide and carbon monoxide, said selectivity adding to the attractiveness of the process.

It is therefore an object of this invention to provide a process for the dehydrogenation of dehydrogenatable hydrocarbons.

A further object of this invention is to provide an oxidative catalytic composition of matter which is used in conjunction with a dehydrogenation catalyst to dehydrogenate dehydrogenatable hydrocarbons to produce a desired product.

In one aspect, an embodiment of this invention resides in a process for the dehydrogenation of a dehydrogenatable hydrocarbon with a hydrogenation catalyst at dehydrogenation conditions in the presence of steam, contacting the resulting mixture of undehydrogenated dehydrogenatable hydrocarbon, resultant dehydrogenated hydrocarbon, hydrogen and steam with an oxygen-containing gas in the presence of an oxidation catalyst comprising a noble metal of Group VIII of the Periodic Table and a metal cation which possesses an ionic radius no less than about 1.35 Angstroms composited on a porous alumina support at oxidation conditions to selectively oxidize hydrogen, and recovering said dehydrogenated hydrocarbons.

A specific embodiment of this invention resides in a process for the dehydrogenation of a dehydrogenatable hydrocarbon which comprises contacting ethylbenzene with a dehydrogenation catalyst at a temperature in the range of from about 500° to about 700° C. and a pressure in the range of from about 0.1 to about 10 atmospheres in the presence of steam, thereafter contacting the resulting mixture of unconverted ethylbenzene, styrene, hydrogen and steam with oxygen in the presence of an oxidation catalyst comprising platinum and cesium composited on an alumina support at a temperature in the range of from about 500° to about 700° C. and a pressure in the range of from about 0.1 to about 10 atmospheres whereby hydrogen is selectively oxidized, and recovering the resultant styrene.

Other objects and embodiments may be found in the following further detailed description of the invention.

DETAILED DESCRIPTION OF THE INVENTION

As hereinbefore set forth, the present invention is concerned with a process for the dehydrogenation of a dehydrogenatable hydrocarbon, the process utilizing both a dehydrogenation catalyst and an oxidation catalyst. The oxidative catalytic compositions of matter which are utilized in the present process will comprise a noble metal of Group VIII of the Periodic Table and a metal cation which possesses an ionic radius no less than about 1.35 Angstroms composited on a porous solid support. Examples of noble metals of Group VIII of the Periodic Table which are utilized in the catalyst will include platinum, palladium, ruthenium, rhodium, osmium and iridium, the preferred metals comprising platinum or palladium. In the preferred embodiment of the invention, the noble metals of the type hereinbefore enumerated will be present on this support in an amount in the range of from about 0.001 to about 5% by weight of the composite. The second component of the oxidative catalytic composition of matter will comprise a metal which possesses an ionic radius of no less than about 1.35 Angstroms. Of these metals, the preferred embodiment of the catalyst will contain either a Group IA or IIA metal which possesses the desired configuration. Specific examples of these Group IA or IIA metals with their ionic radii will include rubidium (1.48 Angstroms), cesium (1.69 Angstroms), barium (1.35 Angstroms), francium (1.76 Angstroms) and radium (1.40 Angstroms). These metal cations which possess the desired ionic radius will be present in an amount in the range of from about 0.01 to about 20% by weight of the said composite.

The aforesaid noble metals of Group VIII of the Periodic Table and the metal cations which possess an ionic radius of no less than about 1.35 Angstroms are composited on a solid support which, in the preferred embodiment of this invention, comprise an alumina which possesses a surface area in the range of from about 1 to about 500 m$^2$/g and which has an Apparent Bulk Density (ABD) of from about 0.1 to about 1.5 g/cc.

In the preferred embodiment of the invention, the metal cations which are used in the oxidation catalyst will comprise rubidium, cesium, and barium and modifiers for the catalyst. While potassium has an ionic radius in proximity to the desired ionic radius, it is not as effective in the capacity as a modifier as are rubidium, cesium and barium. The stability of oxidation catalysts which contain the desired modifiers over the stability of a catalyst containing potassium is due to the fact that the potassium ions are more volatile and will tend to migrate from the surface of the catalyst, thus reducing its effectiveness and contributing to a relative instability of the oxidative catalytic composition of matter. Rubidium and cesium ions are larger and less volatile than the potassium ions because they are heavier. This size and weight contributes to the effectiveness in stabilizing the highly porous solid support such as alumina against structural change under the highly severe hydrothermal conditions which are employed in the dehydrogenation process. While barium ions have approximately the same size, although slightly larger than the potassium ions, the former possess a strong affinity with the surface of the alumina support due to its divalent ion as opposed to potassium which is monovalent. Therefore, barium ions will not only act as an effective stabilizing source to inhibit the structural change of alumina, but will also, due to the aforesaid divalent metal, be more stable against sublimation or volatilization with concurrent less migration than is the potassium ion.

The oxidative catalytic composition of matter of the present invention may be prepared by compositing a noble metal of Group VIII of the Periodic Table and a metal which possesses an ionic radius no less than 1.35 Angstroms on a solid support which, in the preferred embodiment of the invention comprises a porous inorganic oxide such as alumina, which has a surface area in the range of from about 1 to about 500 $m^2/g$ and an ABD of from about 0.3 to about 1.5 g/cc. The preparation is effected by impregnating the alumina, which may be in the form of beads, spheres, pellets, etc. with an aqueous solution of a Group VIII metal compound of the Periodic Table. The aqueous solution of the noble metal-containing compound may be prepared from soluble salts of these metals, such as chloroplatinic acid, chloropalladic acid, ruthenium chloride, rhodium chloride, osmium chloride, iridium chloride, platinum sulfate, palladium sulfate, etc. The solid support is impregnated with the solution for a period of time which is sufficient to allow the deposition of the desired amount of the noble metal on the solid support, that is, an amount sufficient so that the finished catalytic composition will contain from about 0.001 to about 5% by weight of the composite. After recovery of the impregnated solid support, the composite is then dried and calcined at a temperature in the range of from about 500° to about 600° C. or more in an air atmosphere.

The thus formed composite containing a noble metal is then further impregnated with an aqueous solution of a metal which possesses an ionic radius no less than 1.35 Angstroms. While it is contemplated within the scope of this invention that any metal which possesses the desired ionic radius may be employed, in the preferred embodiment of the invention the metal will comprise one which is selected from Groups IA and IIA of the Periodic Table. The impregnation is effected by subjecting the noble metal-containing composite to an impregnation utilizing an aqueous solution containing the desired metal. Examples of salts of these metals which may be employed will include rubidium chloride, rubidium bromide, rubidium iodide, rubidium nitrate, rubidium sulfate, rubidium acetate, rubidium propionate, cesium chloride, cesium bromide, cesium iodide, cesium nitrate, cesium sulfate, cesium acetete, cesium propionate, calcium chloride, barium chloride, barium bromide, barium iodide, barium nitrate, barium sulfate, barium acetate, barium propionate, etc. After allowing the impregnation to proceed for a period of time sufficient to permit the deposition of the desired amount of metal on the catalyst, the composite is recovered, dried, and calcined at a temperature within the range hereinbefore set forth, and recovered.

It is also contemplated within the scope of this invention that the preparation of the oxidative catalytic composition of matter may be prepared by coimpregnating the noble metal and the metal containing an ionic radius no less than 1.35 Angstroms. When such a type of preparation is employed, the solid support, such as gamma-alumina, is impregnated with an aqueous solution containing salts of both the noble metal and the metal possessing an ionic radius of no less than 1.35 Angstroms in a manner similar to that hereinbefore set forth. After allowing the impregnation to proceed for a predetermined period of time, the composite is recovered, dried and calcined at a temperature within the range hereinbefore set forth in an air atmosphere, following which it is recovered for use in a dehydrogenation process hereinafter set forth in greater detail. It is to be understood that the aforementioned noble metal salts and salts of metals possessing an ionic radius of no less than 1.35 Angstroms are only representative of the class of compounds which may be employed to prepare the desired oxidative catalytic compositions of matter, and that the present invention is not necessarily limited thereto.

Examples of oxidative catalytic compositions of matter of the present invention will include platinum and potassium composited on alumina, palladium and potassium composited on alumina, rhodium and potassium composite on alumina, ruthenium and potassium composited on alumina, osmium and potassium composite on alumina, iridium and potassium composited on alumina, platinum and cesium composited on alumina, palladium and cesium composited on alumina, rhodium and cesium composited on alumina, ruthenium and cesium composited on alumina, osmium and cesium composited on alumina, iridium and cesium composited on alumina, platinum and rubidium composite on alumina, palladium and rubidium composited on alumina, rhodium and rubidium composited on alumina, ruthenium and rubidium composited on alumina, osmium and rubidium composited on alumina, iridium and rubidium composited on alumina, platinum and barium composited on alumina, palladium and barium composited on alumina, rhodium and barium composited on alumina, ruthenium and barium composited on alumina, osmium and barium composited on alumina, iridium and barium composited on alumina, etc.

Examples of oxidative catalytic compositions of matter which may be used in the process of the present invention will include platinum and cesium composited on alumina, palladium and cesium composited on alumina, rhodium and cesium composited on alumina, ruthenium and cesium composited on alumina, osmium and cesium composited on alumina, iridium and cesium composited on alumina, platinum and rubidium composited on alumina, palladium and rubidium composited on alumina, rhodium and rubidium composited on alumina, ruthenium and rubidium composited on alumina, osmium and rubidium composited on alumina, iridium and rubidium composited on alumina, platinum and barium composited on alumina, palladium and barium composited on alumina, rhodium and barium composited on alumina, ruthenium and barium composited on alumina, osmium and barium composited on alumina, iridium and barium composited on alumina, etc. It is to be understood that the enumerated catalysts are only representative of the compositions of matter of the present invention and that said invention is not necessarily limited thereto. By utilizing this oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated. This is in contradistinction to prior art types of oxidation catalysts which do not possess the stability of the present catalysts and cannot survive for a long period of time. The relative instability of these catalysts, due to volatility or migration of the catalytically active metals or modifiers, makes the commercial use of such catalysts unattractive due to the necessity of having to replace or regenerate the catalyst after a relatively short interval of operating time has elapsed. In addition, the catalyst which are used in the process of this invention also exhibit a definite affinity for the selective oxidation of hydrogen rather than a tendency for the oxidation of the dehydrogenated product of other compounds which are present in the reaction system such as carbon monoxide or carbon dioxide.

It is contemplated that the dehydrogenation process for the dehydrogenation of dehydrogenatable hydrocarbons utilizing the oxidative catalytic compositions of matter comprising a noble metal of Group VIII of the Periodic Table and a metal cation having an ionic ratio no less than about 1.35 Angstroms will be applicable to a wide variety of dehydrogenatable hydrocarbons. Examples of hydrocarbons which are susceptible to a dehydrogenation process utilizing the catalyst of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnaphthalene, isopropylnapthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as 1-butene, 2-butene, 1-pentene, 2-pentene, 1-hexene, 2-hexene, 3-hexene, and branched chain derivatives thereof, etc.

The dehydrogenation process of the present invention utilizing the oxidative catalytic compositions of matter of the type hereinbefore described in conjunction with a dehydrogenation catalyst may be effected in a variety of ways. One method of effecting the dehydrogenation process utilizes an apparatus in which the dehydrogenation catalyst and the oxidative catalyst are loaded in a reactor in alternative layers. As an illustration, the dehydrogenation zone will contain a dehydrogenation catalyst of the type known in the art. Examples of dehydrogenation catalysts which may be employed will comprise an alkaline metal-promoted iron compound, a typical example of this type of catalyst consisting essentially of 85% by weight of ferric oxide, 2% by weight of chromia, 12% by weight of potassium hydroxide and 1% by weight of sodium hydroxide, while another typical catalyst composition comprises 90% by weight of iron oxide, 4% by weight of chromia and 6% by weight of potassium carbonate. In addition to these catalysts, other well-known dehydrogenation catalysts may be utilized including those comprising ferric oxide, potassium oxide, other metal oxides and/or sulfides including those of calcium, lithium, strontium, magnesium, beryllium, zirconium, tungsten, molybdenum, titanium, hafnium, vanadium, lanthanum, chromium, copper and mixtures of two or more including chromia-alumina, chromia-titania, alumina-vanadia, and the like.

The dehydrogenation of a dehydrogenatable hydrocarbon such as, for example, ethylbenzene, is effected by contacting the dehydrogenatable hydrocarbon and steam with the catalyst at dehydrogenation conditions which are in the range of from about 500° to about 700° C. and at a reaction pressure in the range of from about 0.1 to about 10 atmospheres; the exact dehydrogenation conditions are, however, a function of the particular dehydrogenatable hydrocarbon undergoing dehydrogenation. Other reaction conditions will include Liquid Hourly Space Velocity based on the hydrocarbon charge of from about 0.1 to about 10 hrs$^{-1}$ and steam to hydrocarbon weight ratios ranging from about 1:1 to about 40:1. The number of dehydrogenation zones of the catalyst beds may vary from 1 to about 5 in number and typically may comprise 3 reaction zones; however, the number of zones is not critical to the invention. After contacting the dehydrogenation catalyst with the steam and hydrocarbon, the resulting mixture is passed through the catalyst bed and is contacted with the oxidative catalytic composition of the type hereinbefore described. In addition, an oxygen-containing gas is introduced into the reactor, preferably at a point adjacent to the oxidative catalyst bed. Examples of oxygen-containing bases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidative catalyst whereby hydrogen is selectively oxidized to water with a minimal amount of reaction of oxygen with the hydrocarbons, either unconverted hydrocarbon or dehydrogenated hydrocarbon. The treatment of the product stream is effected under conditions similar to those which are used for the dehydrogenation step of the process, namely, temperature in the range of from about 500° to about 700° C. and pressures in the range of from about 0.1 to about 10 atmospheres.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

Alternatively, the dehydrogenation process may be effected in a single reaction zone in which the dehydrogenation catalyst and the oxidation catalyst are loaded in the reactor in a homogeneously-mixed fashion. The dehydrogenatable hydrocarbon, along with steam, is passed over the homogeneous catalyst at reaction conditions similar to those hereinbefore set forth, while introducing an oxygen-containing gas of the type previously mentioned into the homogeneous catalyst loading. Following the passing of the hydrocarbon through the catalyst bed, the product stream is withdrawn and the desired dehydrogenated hydrocarbon product is separated from unreacted hydrocarbon which may then be recycled to form a portion of the feedstock.

The following examples are given for purposes of illustrating the novel oxidative catalytic compositions of matter and the process of the present invention. However, it is to be understood that these examples are given merely for purposes of illustration and that the present invention is not necessarily limited thereto. All of the tests were conducted at an unusually high space velocity of 100 hrs$^{-1}$ Liquid Hourly Space Velocity of ethylbenzene and styrene feed, inasmuch as all of the catalysts had very high initial activity to achieve a 100% conversion of oxygen. Therefore, the catalytic stabilities could not be differentiated at the standard space velocity in an accelerated stability test.

EXAMPLE I

An oxidative catalytic composition of matter was prepared by impregnating 500 cc of 1/16" diameter gamma-alumina beads which possessed a surface area of 193 m$^2$/g and an ABD of 0.49 g/cc with 500 ml of chloroplatinic acid solution. The chloroplatinic acid solution which contained 0.0493 gram of platinum per ml also contained 2% by weight of hydrochloric acid. After impregnating the alumina with the solution for a period of about 2 hours, the impregnated alumina was dried and calcined at a temperature of 540° C. for a period of 6 hours in the presence of a gas consisting of 50% air and 50% steam. The impregnated composite which was recovered from the calcination step had a surface area of 158 m$^2$/g, a pore volume of 0.51 cc/g and an ABD of 0.68 g/cc.

The platinum impregnated alumina which was prepared according to the above paragraph was impregnated with a 500 ml aqueous solution of potassium nitrate containing 3.63% by weight of potassium nitrate. After impregnating the composite for a period of about 2 hours, the catalyst was recovered, dried and calcined at a temperature of 540° C. for a period of 2 hours. The finished catalytic composite had a surface area of 153 m$^2$/g, a pore volume of 0.41 cc/g and an ABD of 0.522 g/cc, and contained 0.79% by weight of platinum and 2.78% by weight of potassium equaling 0.07 gram-atom per 100 gram catalyst.

The catalyst in an amount of 5.15 cc was loaded into a ⅛" inner diameter stainless steel tubing reactor. The catalyst was treated by feeding a mixture of ethylbenzene, styrene, hydrogen, air, nitrogen and steam which simulated a product stream at about a 60% ethylbenzene conversion from the second dehydrogenation catalyst bed of a 3-dehydrogenation catalyst bed reactor system having oxidation catalyst beds positioned between the dehydrogenation catalyst beds. The feed stream was passed over the oxidation catalyst bed at a temperature of 600° C. and a pressure of 0.5 atmospheres at a Liquid Hourly Space Velocity of 100 hrs$^{-1}$. The molar feed ratio of the feed stream of ethylbenzene:styrene:water:hydrogen:oxygen:nitrogen was 1:1.48:17.9:1.14:0.25:2.21. The conversion of the oxygen was plotted for a period of 300 hours, the results of said run being set forth in Table I below:

TABLE I

| Hours On Stream | % Oxygen Conversion | Δ % Conversion Based on the 50 Hr. On-Stream Conversion |
|---|---|---|
| 50 | 66 | — |
| 100 | 60 | −6 |
| 150 | 60 | −6 |
| 200 | 63 | −3 |
| 250 | 59 | −7 |
| 300 | 58 | −8 |

EXAMPLE II

In like manner, a catalyst comprising platinum and potassium composited on alumina was prepared by impregnating 500 cc of 1/16" diameter gamma-alumina beads with an aqueous chloroplatinic acid solution at about 100° C. The alumina was impregnated for a period of 2 hours following which the impregnated alumina was dried and calcined at a temperature of about 540° C. for a period of 2 hours in the presence of a gas consisting of a mixture of air and steam. The impregnated sample was then further impregnated with an aqueous solution of potassium nitrate at about 100° C. for 2 hours following which the sample was recovered, dried and calcined at 540° C. for 2 hours. The impregnated composite which was recovered from the calcination step contained 0.79% by weight of platinum and 2.78% by weight of potassium. In addition the composite had a surface area of 152 m$^2$/g, a pore volume of 0.41 cc/g, and an ABD of 0.522 g/cc.

The catalyst was loaded into a ⅜" inner diameter stainless steel tube reactor having a 10" long ½" diameter bore for the catalyst loading. The reactor was heated to an inlet temperature of 600° C. and a feed stream comprising a mixture of ethylbenzene, styrene, steam, hydrogen, oxygen and nitrogen which simulated a product stream at about a 60% ethylbenzene conversion from the second dehydrogenation catalyst bed of a 3-dehydrogenation catalyst bed reactor system having an oxidation catalyst bed positioned between the dehydrogenation catalysts beds, was fed to the reactor. The feed stream was passed over the oxidation catalyst bed at the aforesaid inlet temperature and a pressure of 0.5 atmospheres at a Liquid Hourly Space Velocity of 100 hrs$^{-1}$. The molar feed ratio of the feed stream of ethylbenzene/styrene/steam/hydrogen/oxygen/nitrogen was 1/1.48/17.9/1.14/0.25/2.21. The conversion of the oxygen was plotted for a period of 250 hours, the results of said run being set forth in Table II below. In this table, column A is the % conversion of oxygen and column B is the mole % selectivity for oxygen reacting to form carbon dioxide and carbon monoxide.

TABLE II

| Hours On Stream | A | B |
|---|---|---|
| 50 | 65 | 26 |
| 100 | 65 | 23 |
| 150 | 66 | 24 |
| 200 | 63 | 23 |
| 250 | 59 | 21 |

EXAMPLE III

In a manner similar to that hereinbefore set forth, a catalyst comprising platinum and a metal cation having an ionic radius no less than about 1.35 Angstroms was prepared by impregnating 240 cc of gamma-alumina beads having 1/16" diameter and possessing the physical characteristics of a surface area of 193 m²/g, a pore volume of 0.58 cc/g, and an ABD of 0.49 g/cc, with 240 ml of an aqueous solution containing 0.0493 gram of platinum per ml. Upon completion of the impregnation, the impregnated support was dried and calcined at a temperature of about 540° C. for a period of 6 hours in a gas stream which consisted of 50% air and 50% steam.

The desired catalytic composite was obtained by impregnating 150 cc of the platinum-impregnated alumina with 150 ml of an aqueous cesium acetate solution containing 3.62% by weight of cesium acetate. Upon completion of the impregnation step, which was effected for a period of about 2 hours, the composite was dried and calcined at a temperature of 500° C. for a period of 2 hours. The resulting catalyst, which had an ABD of 0.52 g/cc and a surface area of 167 m²/g, contained 0.77% by weight of platinum and 3.9% by weight of cesium equaling 0.03 gram-atom per 100 gram catalyst.

As in the above example, 5.15 cc of this catalyst was loaded into a ⅛" inner diameter stainless steel tubing reactor and treated with a feed mixture comprising ethylbenzene, styrene, hydrogen, air, nitrogen and steam, said feed mixture simulating a product stream resulting from the treatment of ethylbenzene with a dehydrogenation catalyst. The feed stream was passed over the oxidation catalyst bed at an inlet temperature of 600° C., a pressure of 0.5 atmospheres at a Liquid Hourly Space Velocity of 100 hrs$^{-1}$. The molar feed ratio of the components of the feed mixture was similar to that set forth in Example I above. The conversion of oxygen is set forth in Table III below:

TABLE III

| Hours On Stream | % Oxygen Conversion | Δ % Conversion Based on the 50 Hr. On-Stream conversion |
|---|---|---|
| 50 | 56 | |
| 100 | 57 | +1 |
| 150 | 58 | +2 |

EXAMPLE IV

To illustrate the advantage of utilizing a metal cation as an ionic radius, no less than about 1.35 Angstroms, two catalyst compositions were prepared utilizing in one instance a potassium as a modifier and in the other instance barium as a modifier. The catalysts were prepared by impregnating alumina beads with an aqueous solution containing platinum. After completing the impregnation with the catalyst, the impregnated support was dried and calcined at a temperature of 540° C. for a period of 6 hours in a gas stream which consisted of 50% air and 50% steam.

In the first instance, the impregnated catalyst was further impregnated with an aqueous solution of potassium nitrate. After impregnating the composite for a period of about 2 hours, the catalyst was recovered, dried and calcined at a temperature of 540° C. for a period of 2 hours. The finished catalytic composite contained 0.19% by weight of platinum and 0.38% by weight of potassium, the composite having a surface area of less than 10 m²/g and an ABD of 1.39 g/cc. This composite was labeled A.

In the second instance, the platinum-impregnated alumina was further impregnated with an aqueous barium solution for a period of 2 hours. Following this, the composite was dried and calcined, the resulting catalyst, which had similar physical characteristics, that is, a surface area of less than 10 m²/g and an ABD of 1.39 g/cc contained 0.19% by weight of platinum and 0.12% by weight of barium. This catalyst was designated B.

As in the above examples, the catalysts were loaded into a ⅛" inner diameter stainless steel tubing reactor and treated with a feed mixture comprising ethylbenzene, styrene, hydrogen, air, nitrogen and steam, said feed mixture simulating a product stream resulting from the treatment of ethylbenzene with a dehydrogenation catalyst. The feed stream which had a molar feed ratio similar to the components of the feed mixture set forth in Example I above, was passed over the oxidation bed at an inlet temperature of 600° C. and an outlet pressure of 0.5 atmospheres at a Liquid Hourly Space Velocity of 100 hrs$^{-1}$. The conversion of oxygen and a selectivity to carbon dioxide, carbon monoxide and hydrogen is set forth in Table IV below:

TABLE IV

| | CATALYST A | | CATALYST B | |
|---|---|---|---|---|
| Hrs. On Stream | % Oxygen Conversion | % Oxygen Selectivity to CO₂ & CO | % Oxygen Conversion | % Oxygen Selectivity to CO₂ & CO |
| 10 | 48 | 15 | 90 | 18 |
| 20 | 35 | 15 | 86 | 18 |
| 50 | 27 | 10 | 80 | 17 |
| 100 | 28 | 10 | 52 | 15 |

It is apparent from the above Table that the presence of barium as a modifier for the oxidative catalyst results in a higher conversion of oxygen than potassium.

EXAMPLE V

In this example, a catalyst similar in nature to those hereinbefore set forth was prepared by impregnating gamma-alumina beads, possessing similar physical characteristics to those hereinbefore set forth, with a chloroplatinic acid solution followed by drying and calcining under similar conditions. The platinum impregnated alumina was then further impregnated with an aqueous solution of sodium nitrate following which the composite was dried and calcined. The finished catalyst composite contained 0.75% platinum and 1.64% sodium, the 1.64 weight % sodium equaling 0.07 gram-atom per 100 gram catalyst. The ionic radius of sodium is 0.95 Angstrom, which is considerably less than the desired 1.35 Angstroms ionic radius of the components of catalysts of the present invention.

The catalyst was then loaded into a stainless steel tubular reactor having a ⅛" inner diameter. A feed stream comprising a mixture of ethylbenzene, styrene, hydrogen, oxygen, nitrogen, and steam in a molar feed ratio identical to those hereinbefore set forth was passed over the catalyst bed at a temperature of 600° C., a pressure of 0.5 atmospheres at a Liquid Hourly Space Velocity of 100 hrs$^{-1}$. The oxygen conversion was plotted for a period of 300 hours, the results of said run being set forth in Table V below:

TABLE V

| Hours On Stream | % Oxygen Conversion | Δ % Conversion Based on the 50 Hour On-Stream Conversion |
|---|---|---|
| 50 | 86 | |
| 100 | 79 | −7 |
| 150 | 75 | −11 |
| 200 | 69 | −17 |
| 250 | 64 | −22 |

TABLE V-continued

| Hours On Stream | % Oxygen Conversion | Δ % Conversion Based on the 50 Hour On-Stream Conversion |
|---|---|---|
| 300 | 59 | −27 |

A comparison of the results set forth in Table V with the results set forth in Tables II and IV above disclosed that the stability of a catalyst which does not contain a metal cation having an ionic radius greater than 1.35 Angstroms is considerably less than the stability of those catalysts which do contain a metal cation such as cesium which possesses the desired ionic radius, the oxygen conversion dropping considerably during a 300 hour run. This is in contradistinction to the stability of the catalysts of the present invention which maintain a stable conversion over a similar period.

EXAMPLE VI

In this example, an oxidation catalyst which contained only platinum impregnated on a solid support was prepared by impregnating 240 cc of gamma-alumina beads which had a surface area of 193 m$^2$/g and an ABD of 0.49 g/cc with 240 ml of a chloroplatinic acid solution containing 0.0493 gram of platinum per ml as well as 2% by weight of hydrochloric acid based on the weight of the alumina. After the impregnation, the beads were dried and calcined at a temperature of 540° C. for a period of 6 hours in the presence of a gas consisting of about 50% air and 50% steam. The finished catalyst composite, which had a surface area of 158 m$^2$/g and an ABD of 0.68 g/cc contained 76% by weight of platinum.

The thus prepared catalyst was utilized as an oxidative catalyst in treating a feed stream consisting of a mixture of ethylbenzene, styrene, water, hydrogen, oxygen, and nitrogen, the molar feed ratio of ethylbenzene:styrene:water:hydrogen:oxygen:nitrogen being 1:1.48:17.9:1.14:0.25:2.21. The feed stream was placed over the catalyst which was placed in the stainless steel tubing at an inlet temperature of 600° C., a pressure of 0.5 atmospheres, at a Liquid Hourly Space Velocity of 100 hrs$^{-1}$. The results of this test which was terminated at 75 hours are set forth in Table VI below:

TABLE VI

| Hours On Stream | % Oxygen Conversion | Δ % Conversion Based on the 25 Hour On-Stream Conversion |
|---|---|---|
| 25 | 48 | |
| 50 | 34 | −14 |
| 75 | 22 | −26 |

It is therefore apparent that an oxidation catalyst containing only a noble metal of Group VIII of the Periodic Table such as platinum composited on alumina without the presence of a metal cation which possesses an ionic radius greater than 1.35 Angstroms exhibits a very poor stability when utilized in the oxidative reaction of the present invention.

EXAMPLE VII

To illustrate the disadvantages of utilizing a metal cation which possesses an ionic radius less than about 1.35 Angstroms, a comparative test was conducted to illustrate the relative volatility of potassium when used as a modifier for the oxidation catalyst compared with barium as a modifier for the catalyst. Two oxidation catalysts were prepared in a manner similar to that set forth in the above examples, each catalyst containing 0.75% by weight of platinum composited on an alumina base. Catalyst A was modified by the presence of 3.0% by weight of potassium while catalyst B was modified by the presence of 3.0% by weight of barium. In each test, 100 cc of the catalysts was loaded in 4 sections or beads of 25 cc each and the entire catalyst system was placed above 50 cc of gamma-alumina spheres. The catalysts were tested for 150 hours employing an inlet temperature of 700° C. and an outlet pressure of 0.5 atmospheres using a feed steam consisting of 576 g/hr of water in the form of steam and 1.6 SCFH of hydrogen. Upon completion of the tests, the catalysts were analyzed to determine the volatility and migration of the potassium and barium. The results are set forth in Table VII below:

TABLE VII

| | Fresh | Catalyst Bed 1 | Catalyst Bed 2 | Catalyst Bed 3 | Catalyst Bed 4 | Al$_2$O$_3$ Bed |
|---|---|---|---|---|---|---|
| | | CATALYST A | | | | |
| Wt. % K | 3.0 | 2.91 | 2.71 | 2.78 | 2.76 | 0.16 |
| Wt. % Pt | 0.749 | 0.749 | 0.751 | 0.744 | 0.751 | <0.01 |
| | | CATALYST B | | | | |
| % Barium | 3.00 | 2.91 | 2.94 | 2.98 | 2.96 | <0.003 |
| % Platinum | 0.755 | 0.763 | 0.756 | 0.761 | 0.760 | <0.01 |

It is noted from the above table that the potassium modified catalyst had lost 6.9 wt. % of its original potassium content, 19% of this lost potassium being absorbed by the alumina bed. In contrast to this, the catalyst which was modified with barium lost only 0.9 wt. % of the original barium content, of which a negligible amount was absorbed by the alumina bed. It is therefore apparent that barium is considerably less volatile than is potassium under the hydrothermal treating conditions which are utilized in a dehydrogenation reaction and will not migrate from the surface of the catalyst. The greater stability of barium thus illustrates the contribution of a modifier of the type of the present invention to the greater activity of an oxidation catalyst which contains modifiers possessing the desired ionic radius, i.e. no less than about 1.35 Angstroms.

I claim as my invention:

1. A process for the dehydrogenation of a dehydrogenatable hydrocarbon which comprises contacting said dehydrogenatable hydrocarbon with a dehydrogenation catalyst at dehydrogenation conditions in the presence of steam, contacting the resulting mixture of undehydrogenated dehydrogenatable hydrocarbon, resultant dehydrogenated hydrocarbon, hydrogen and steam with an oxygen-containing gas in the presence of an oxidation catalyst comprising a noble metal of Group VIII of the Periodic Table and a metal cation which possesses an ionic radius no less than about 1.35 Angstroms selected from the group consisting of rubidium, cesium, barium, francium and radium composited on a porous alumina support at oxidation conditions to selectively oxidize hydrogen, and recovering said dehydrogenated hydrocarbon.

2. The process as set forth in claim 1 in which said alumina has a surface area of from about 1 to about 500 m$^2$/g and an ABD of from about 0.1 to about 1.5 g/cc.

3. The process as set forth in claim 1 in which said noble metal of Group VIII of the Periodic Table is present in said composite in an amount in the range of from about 0.001 to about 5% by weight of said composite.

4. The process as set forth in claim 1 in which said metal cation is present in said composite in an amount in the range of from about 0.01 to about 20% by weight of said composite.

5. The process as set forth in claim 1 in which said dehydrogenation conditions include a temperature in the range of from about 500° to about 700° C. and a pressure in the range of from about 0.1 to about 10 atmospheres.

6. The process as set forth in claim 1 in which said oxidation conditions include a temperature in the range of from about 500° to about 700° C. and a pressure in the range of from about 0.1 to about 10 atmospheres.

7. The process as set forth in claim 1 in which said oxygen-containing gas is oxygen.

8. The process as set forth in claim 1 in which said oxygen-containing gas is air.

9. The process as set forth in claim 1 in which said noble metal of Group VIII of the Periodic Table is platinum.

10. The process as set forth in claim 1 in which said noble metal of Group VIII of the Periodic Table is palladium.

* * * * *